(12) United States Patent
Inoue et al.

(10) Patent No.: US 7,611,468 B2
(45) Date of Patent: *Nov. 3, 2009

(54) BLOOD PRESSURE MEASUREMENT CUFF WRAPPING CONTROL DEVICE AND METHOD

(75) Inventors: Tomonori Inoue, Kyoto (JP); Yoshihiko Sano, Kyoto (JP); Takahide Tanaka, Kyoto (JP); Yukiya Sawanoi, Kyoto (JP); Minoru Taniguchi, Kyoto (JP); Hiroya Nakanishi, Kyoto (JP); Takefumi Nakanishi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 202 days.

This patent is subject to a terminal disclaimer.

(21) Appl. No.: 11/109,733

(22) Filed: Apr. 20, 2005

(65) Prior Publication Data

US 2005/0240109 A1  Oct. 27, 2005

(30) Foreign Application Priority Data

Apr. 26, 2004  (JP) ............................. 2004-129977

(51) Int. Cl.
*A61B 5/00* (2006.01)
(52) U.S. Cl. .................. 600/490; 600/493; 600/499
(58) Field of Classification Search ......... 600/490–503, 600/485, 481, 483
See application file for complete search history.

(56) References Cited

U.S. PATENT DOCUMENTS

| | | | |
|---|---|---|---|
| 3,527,204 A | | 9/1970 | Lern |
| 3,935,984 A * | | 2/1976 | Lichowsky et al. ......... 600/499 |
| 4,206,765 A | | 6/1980 | Huber |
| 4,274,424 A * | | 6/1981 | Kimura et al. .............. 600/499 |
| 4,605,010 A | | 8/1986 | McEwen |
| 4,995,399 A * | | 2/1991 | Hayashi et al. ............. 600/493 |
| 5,069,219 A * | | 12/1991 | Knoblich ..................... 600/492 |
| 5,595,180 A * | | 1/1997 | Ogura et al. ................. 600/499 |
| 6,228,035 B1 * | | 5/2001 | Packman et al. ............ 600/485 |
| 6,251,081 B1 * | | 6/2001 | Narimatsu ................... 600/490 |
| 7,008,379 B2 * | | 3/2006 | Takahashi et al. ........... 600/490 |

(Continued)

FOREIGN PATENT DOCUMENTS

EP  0696433 A1  2/1996

(Continued)

OTHER PUBLICATIONS

European Search Report dated Aug. 5, 2005, directed to corresponding foreign application.

*Primary Examiner*—Robert L Nasser
(74) *Attorney, Agent, or Firm*—Morrison & Foerster LLP

(57) ABSTRACT

In wrapping a blood pressure measurement cuff enclosing therein a bladder, which is inflated when supplied with air, around a region for measurement, first, a predetermined amount of air is supplied to the bladder and then enclosed therein. Then, the blood pressure measurement cuff is wrapped around the region for measurement of a subject for the purpose of measuring his/her blood pressure. During this wrapping process, relative variations in the pressure in the bladder are sequentially detected. The time period in which the detection results indicate that the variation has not reached a predetermined threshold value, the wrapping proceeds. When the detection results indicate that the variation has reached the predetermined threshold value, the wrapping is terminated.

12 Claims, 15 Drawing Sheets

U.S. PATENT DOCUMENTS 7,118,535 B2 * 10/2006 Sawanoi et al. ............. 600/490

FOREIGN PATENT DOCUMENTS

| | | |
|---|---|---|
| EP | 1075846 A2 | 2/2001 |
| JP | 59-181128 A | 10/1984 |
| JP | 06-237906 | 8/1994 |
| JP | 2001-204695 A | 7/2001 |
| WO | WO-91/08705 A1 | 6/1991 |

* cited by examiner

BLOOD PRESSURE MEASUREMENT CUFF WRAPPING CONTROL DEVICE AND METHOD

BACKGROUND OF THE INVENTION

1. Field of the Invention

The present invention relates to devices and method for controlling wrapping of a blood pressure measurement cuff including a bladder around a region for measurement of a living body. More particularly, the present invention relates to blood pressure measurement cuff wrapping control devices and method for making the strength of wrapping around the region for measurement to be appropriate.

2. Description of the Background Art

In conventional electronic blood pressure measurement devices, a measurement cuff including a bladder is wrapped around a region for measurement of a living body in advance for blood pressure measurements. However, the strength of wrapping, namely the degree of pressurization on the living body caused by the wrapping, has not been grasped, thereby making it difficult to prescribe a proper wrapping strength. In order to overcome the problem, there has been suggested, for example, a method disclosed in Japanese Laid-Open Patent Publication No. 6-237906. This publication discloses a configuration for enclosing gas within a bladder, in advance, and then wrapping it around a region for measurement. Further, the publication prescribes that a proper wrapping condition has been achieved when the pressure of gas within the bladder reaches a predetermined pressure.

However, with the configuration disclosed in this publication, in the case where the amount of air enclosed within the bladder or the size of the bladder is changed, this will change the pressure applied to the artery in the region for measurement and therefore the predetermined pressure must be altered to a proper pressure in association therewith.

Further, since the same preset pressure is applied to all subjects for blood pressure measurement, there has been inconvenience that, even when it is determined that a proper wrapping condition is achieved, the setting of wrapping will be tight for subjects having a thicker arm which is the region for measurement, while it will be loose for subjects having a thinner arm. Also, in the case where the measurement cuff is to be manually wrapped around the region for measurement, the subject can not know the required wrapping strength (the pressurization level), thus preventing proper blood pressure measurements.

SUMMARY OF THE INVENTION

It is an object of the present invention to provide blood pressure measurement cuff wrapping control devices and method which enable properly wrapping a blood pressure measurement cuff around a region for measurement.

A device according to an aspect of the present invention wraps a blood pressure measurement cuff including a bladder, which is inflated when supplied with fluid, around a region for measurement. The device includes a fluid enclosure portion for supplying a predetermined amount of fluid to the bladder and enclosing it therein in wrapping, and a pressure variation detection portion for detecting whether or not a relative variation in the pressure in the bladder has reached a predetermined level during the wrapping of the blood pressure measurement cuff in which the fluid has been enclosed by the fluid enclosure portion, around the region for measurement for blood pressure measurements.

Therefore, the pressure variation detection portion detects whether or not a relative variation in the pressure in the bladder has reached a predetermined level during the wrapping of the blood pressure measurement cuff around the region for measurement. By setting the predetermined level to a proper level for blood pressure measurement and referring thereto, it can be detected that the wrapping state has become appropriate for blood pressure measurement, based on relative variations in the pressure within the bladder, regardless of the circumferential length of the region for measurement and regardless of the size or the capacity of the bladder.

Preferably, the device further includes a wrapping stop operation portion for performing an operation for stopping the wrapping of the blood pressure measurement cuff when the pressure variation detection portion detects that the relative variation has reached the predetermined level.

Therefore, when the pressure variation detection portion detects that the relative variation in the pressure in the bladder has reached the predetermined level during the wrapping of the blood pressure measurement cuff around the region for measurement, it is determined that the wrapping state has become appropriate for blood pressure measurements and the wrapping stop operation portion performs the operation for stopping the wrapping of the blood pressure measurement cuff.

Preferably, the wrapping stop operation portion includes a portion for giving an instruction for stopping the wrapping to the outside. Therefore, in the case where the wrapping is manually performed, the subject is informed that the wrapping state has become appropriate for blood pressure measurements, since an instruction for stopping the wrapping is given to the outside. Thus, the subject can cease the manual wrapping operation when the wrapping state has become appropriate for blood pressure measurements. Consequently, the subject will be released from stress caused by the determination of the time point at which the wrapping should be stopped, thus enabling accurate blood pressure measurements. Also, in the case of automatically-wrapping type device, the subject can know that the wrapping state has become appropriate for blood pressure measurements and the subsequent pressurization step is entered, since an instruction that the wrapping state has become appropriate for blood pressure measurements is given to the outside.

Preferably, the pressure variation detection portion includes an enclosure pressure detection portion for detecting the pressure within the bladder when the blood pressure measurement cuff is wrapped around the region for measurement after the fluid is enclosed within the bladder by the fluid enclosure portion, a wrapping pressure detection portion for sequentially detecting the pressure within the bladder during further wrapping the blood pressure measurement cuff around the region for measurement after the enclosure pressure detection portion detects the pressure, and a determination portion for determining, each time the wrapping pressure detection portion detects the pressure, whether or not the difference between this detected pressure and the pressure detected by the enclosure pressure detection portion has reached the predetermined level.

Therefore, the difference between the pressure within the bladder when the blood pressure measurement cuff is wrapped and mounted around the region for measurement after the fluid is enclosed therein and the pressure in the bladder which is sequentially detected during further wrapping the blood pressure measurement cuff around the region for measurement reaches the predetermined level, it can be detected that the wrapping state has become appropriate for blood pressure measurements.

Preferably, the pressure variation detection portion includes a wrapping pressure detection portion for sequentially detecting the pressure within the bladder during further wrapping the blood pressure measurement cuff around the region for measurement for blood pressure measurements after the fluid is enclosed in the bladder by the fluid enclosure portion and then the blood pressure measurement cuff is wrapped and mounted around the region for measurement, and a determination portion for determining whether or not the variation per unit time in the pressure detected by the wrapping pressure detection portion has reached the predetermined level.

Therefore, during wrapping after the fluid is enclosed and then the blood pressure measurement cuff is wrapped and mounted around the region for measurement, when the variation per unit time in the pressure within the bladder, which is sequentially detected, has reached the predetermined level, it can be detected that the wrapping state has become appropriate for blood pressure measurements.

Preferably, the determination portion includes a portion for determining whether or not the variation per unit time in the pressure detected by the wrapping pressure detection portion has reached a maximum.

Therefore, during wrapping after the fluid is enclosed and then the blood pressure measurement cuff is wrapped and mounted around the region for measurement, when the variation per unit time in the pressure within the bladder, which is sequentially detected, has reached a maximum, it can be detected that the wrapping state has become appropriate for blood pressure measurements.

Preferably, the blood pressure measurement cuff is manually wrapped around the region for measurement such that the wrapping size thereof in a radial direction for the region for measurement is reduced.

Therefore, the aforementioned process for detecting that the wrapping state has become appropriate for blood pressure measurements may be applied for cases where the blood pressure measurement cuff is manually wrapped around the region for measurement.

Preferably, the tension in the blood pressure measurement cuff is increased such that the wrapping size thereof in a radial direction for the region for measurement is reduced.

Therefore, the aforementioned process for detecting that the wrapping state has become appropriate for blood pressure measurements may be applied for cases where the blood pressure measurement cuff is wrapped around the region for measurement through the tension therein.

Preferably, the wrapping size of the blood pressure measurement cuff in a radial direction for the region for measurement is reduced by the effect of the inflation of a securing bag, wherein the securing bag is inflated when supplied with fluid in order to press the bladder for securing the bladder.

Therefore, the aforementioned process for detecting that the wrapping state has become appropriate for blood pressure measurements may be applied for cases where the blood pressure measurement cuff is wrapped around the region for measurement through the inflation force of a securing bag.

Preferably, the device includes a circumferential length detection portion for detecting the circumferential length of the region for measurement, and a predetermined level determination portion for determining the predetermined level based on the circumferential length detected by the circumferential length detection portion.

Therefore, the predetermined level which is referred for determining whether or not the wrapping state has become appropriate for blood pressure measurements may be variably set based on the circumferential length of the region for measurement. Thus, it can be more accurately detected that the wrapping state has become appropriate.

A method for controlling wrapping of a blood pressure measurement cuff including a bladder, which is inflated when supplied with fluid, around a region for measurement, according to another aspect of the present invention, includes a fluid enclosure step of supplying a predetermined amount of fluid to the bladder and enclosing it therein for wrapping, and a pressure change detection step of detecting whether or not a relative variation in the pressure in the bladder has reached a predetermined level during wrapping the blood pressure measurement cuff around the region for measurement for blood pressure measurements, after the fluid is enclosed in the bladder in the fluid enclosure step.

Therefore, in the pressure change detection step, it is detected whether or not a relative change in the pressure in the bladder has reached a predetermined level during the wrapping of the blood pressure measurement cuff around the region for measurement. By setting the predetermined level to a proper level for blood pressure measurement and referring thereto, it can be detected that the wrapping state has become appropriate for blood pressure measurement, based on relative variations in the pressure within the bladder, regardless of the circumferential length of the region for measurement and regardless of the size or the capacity of the bladder.

Preferably, the method further includes a wrapping stop operation step of performing an operation for stopping the wrapping of the blood pressure measurement cuff around the region for measurement, when it is detected that the relative variation has reached the predetermined level in the pressure change detection step.

Therefore, when it is detected in the pressure change detection step that the relative variation in the pressure in the bladder has reached the predetermined level during the wrapping of the blood pressure measurement cuff around the region for measurement, it is determined that the wrapping state has become appropriate for blood pressure measurements and, in the wrapping stop operation step, an operation for stopping the wrapping of the blood pressure measurement cuff is performed.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Hereinafter, embodiments of the present invention will be described with reference to the drawings. An electronic blood pressure measurement device according to the present invention may utilize either a blood-pressure measuring method according to the oscillometric method or a measuring method using Korotkoff sound.

It is assumed, in the present embodiment, that the electronic blood pressure measurement device is a manually-wrapping type electronic blood pressure measurement device and an automatic-wrapping type electronic blood pressure measurement device both including a cuff which is a bag containing fluid such as air and is to be wrapped around a region for measurement for blood pressure measurements. Such a manually-wrapping type electronic blood pressure measurement device is configured such that a subject manually wraps the cuff around the region for measurement while reducing the wrapping size in a radial direction, while such an automatic-wrapping type electronic blood pressure measurement device is configured such that the cuff is automatically wrapped around the region for measurement. Further, it is assumed, in the present embodiment, that the cuff is a bladder and the region for measurement around which the cuff is to be wrapped is an arm. However, the region for measurement is not limited to an arm.

Further, in the present embodiment, as an automatically-wrapping type electronic blood pressure measurement device, there will be exemplified an electronic blood pressure measurement device which wraps a blood pressure measurement bladder around an arm through the effect of the inflation of a pressing-securing air bag. However, the present invention is not limited to this. For example, instead of a pressing-securing air bag, a mechanically-stretchable mechanism may be used to vary the distance between the living body and the blood pressure measurement bladder for wrapping the blood pressure measurement bladder around the arm. Also, as in Japanese Laid-Open Patent Publication No. 6-237906, an arm cuff may be wrapped around the region for measurement through the tension of the arm cuff induced by securing one end of the arm cuff while causing the other end thereof to be pulled in conjunction with the rotation of a motor.

Figure 1:
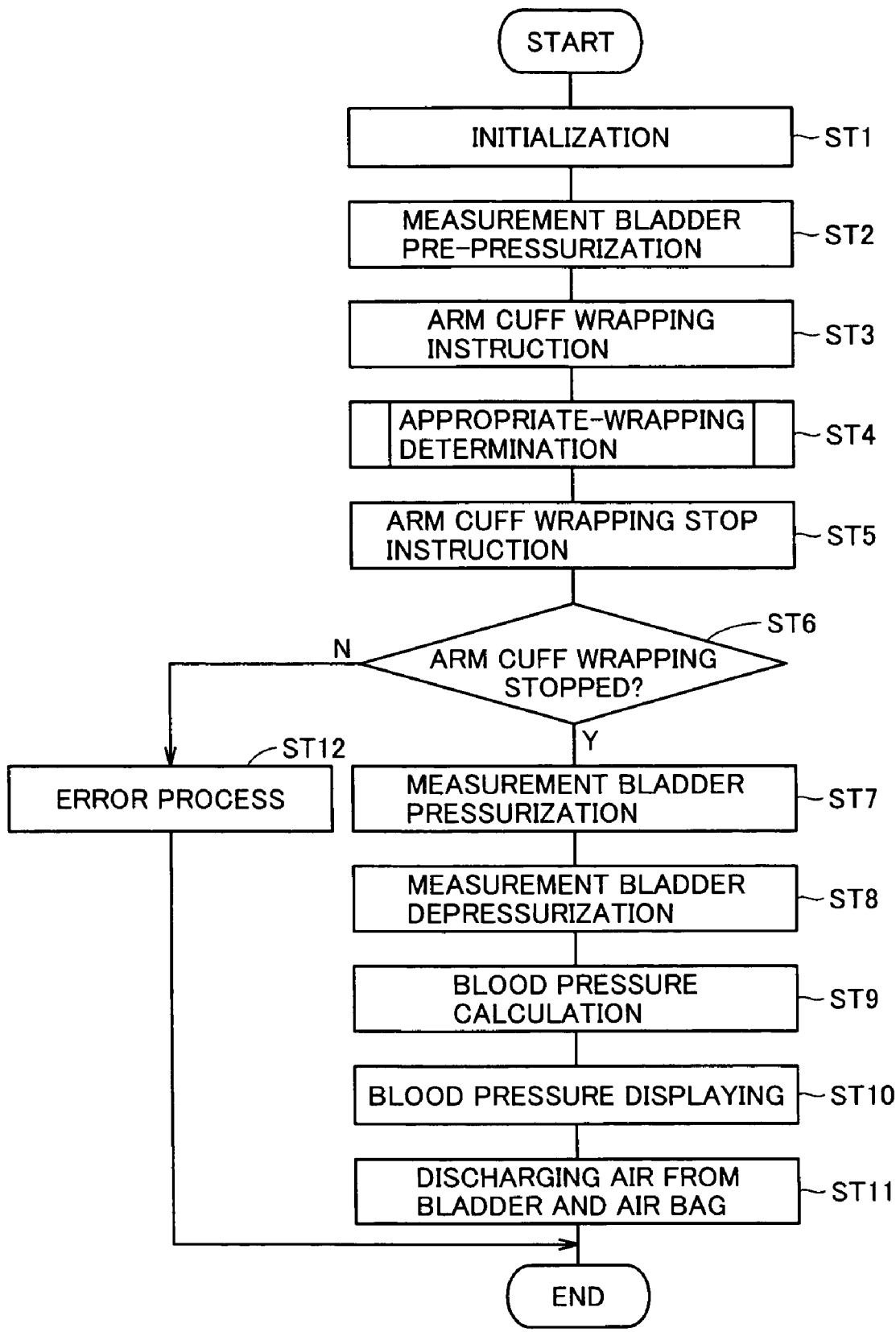
FIG. 1 is a flowchart of blood pressure measurement which is common to a manually-wrapping type and automatically-wrapping type electronic blood pressure measurement devices according to an embodiment of the present invention.
Figure 2:
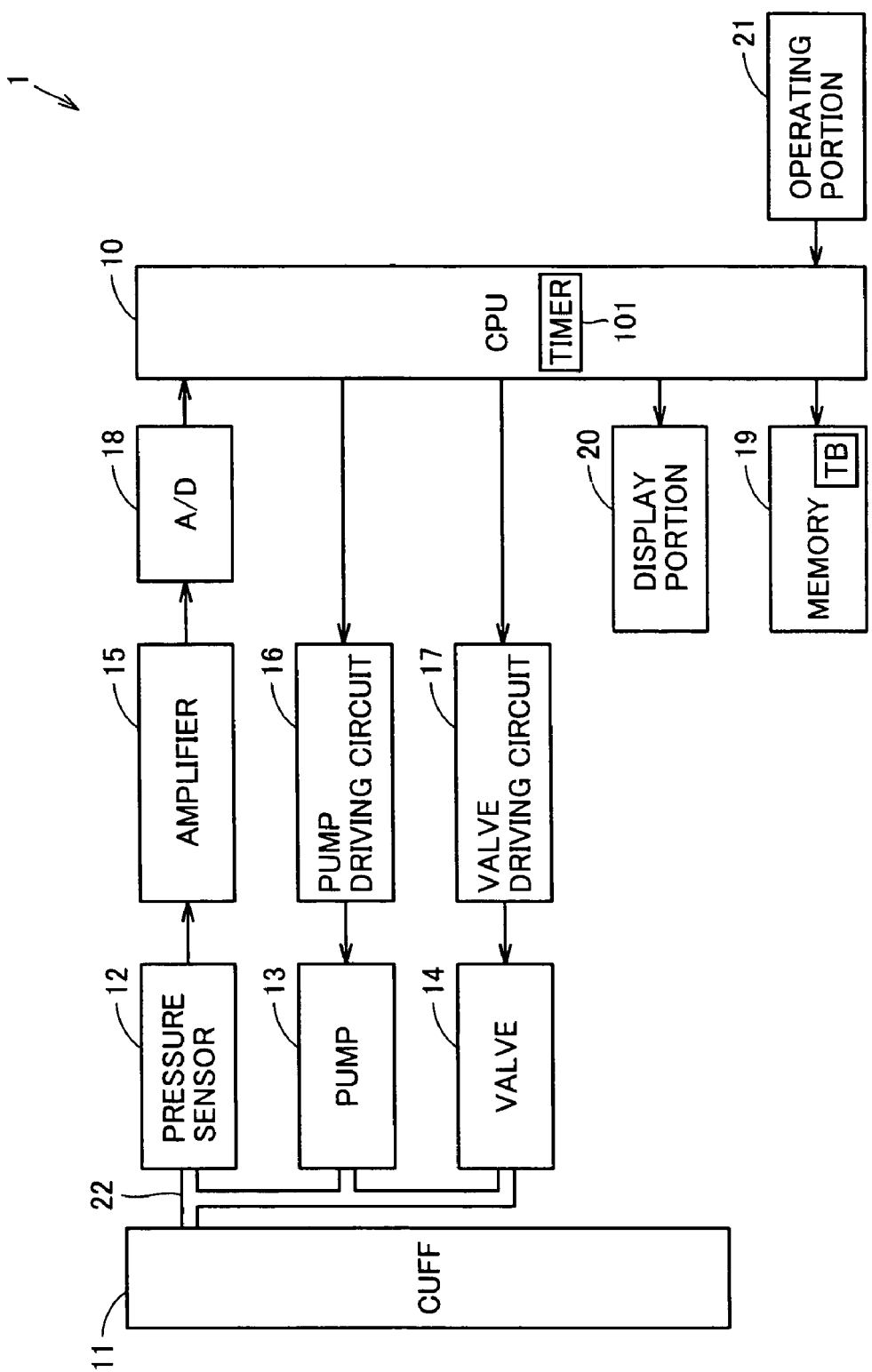
FIG. 2 is a block diagram of the manually-wrapping type electronic blood pressure measurement device applied to an embodiment of the present invention.
Figure 3:
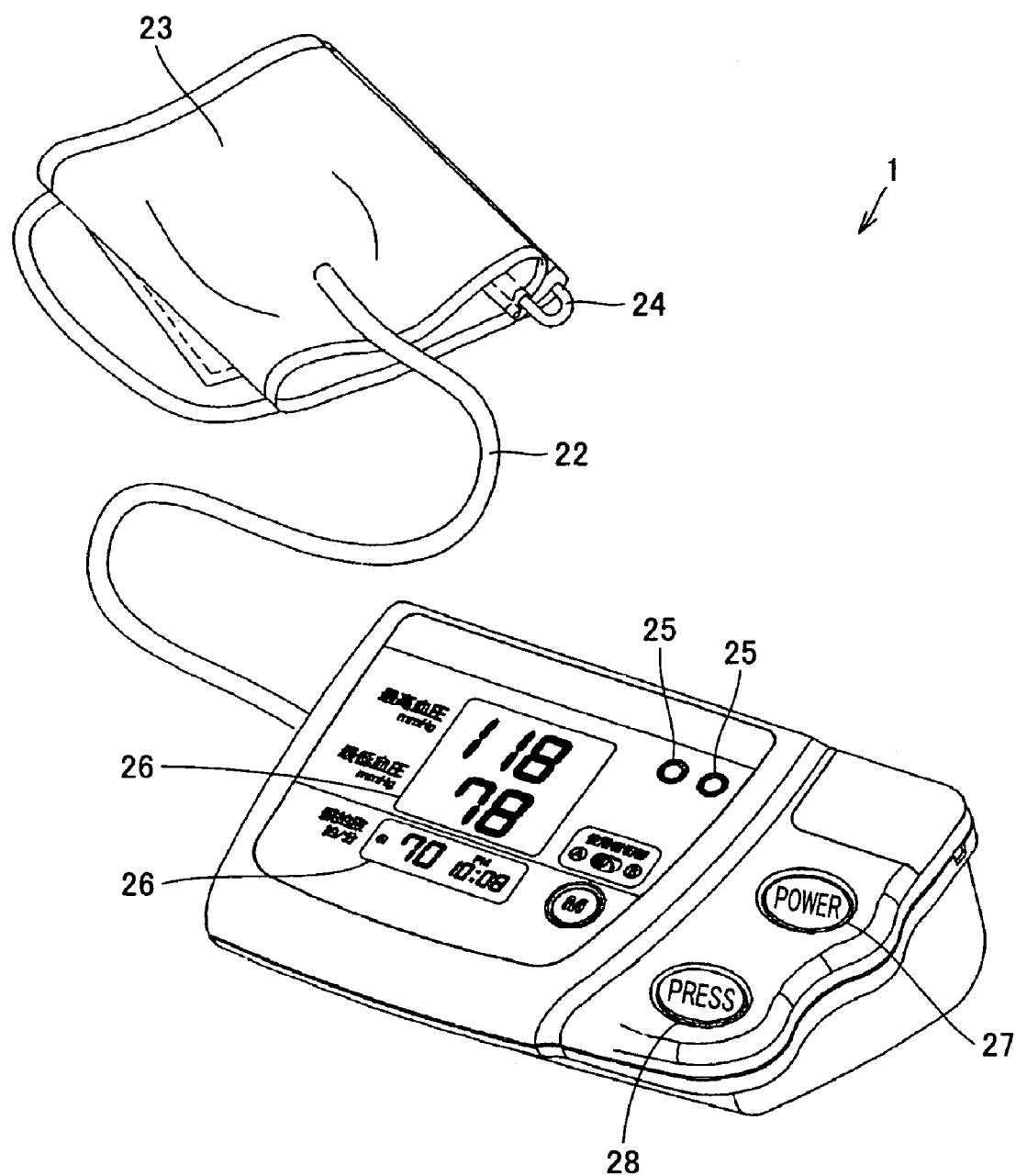
FIG. 3 shows an external view of the manually-wrapping type electronic blood pressure measurement device.
Figure 4:
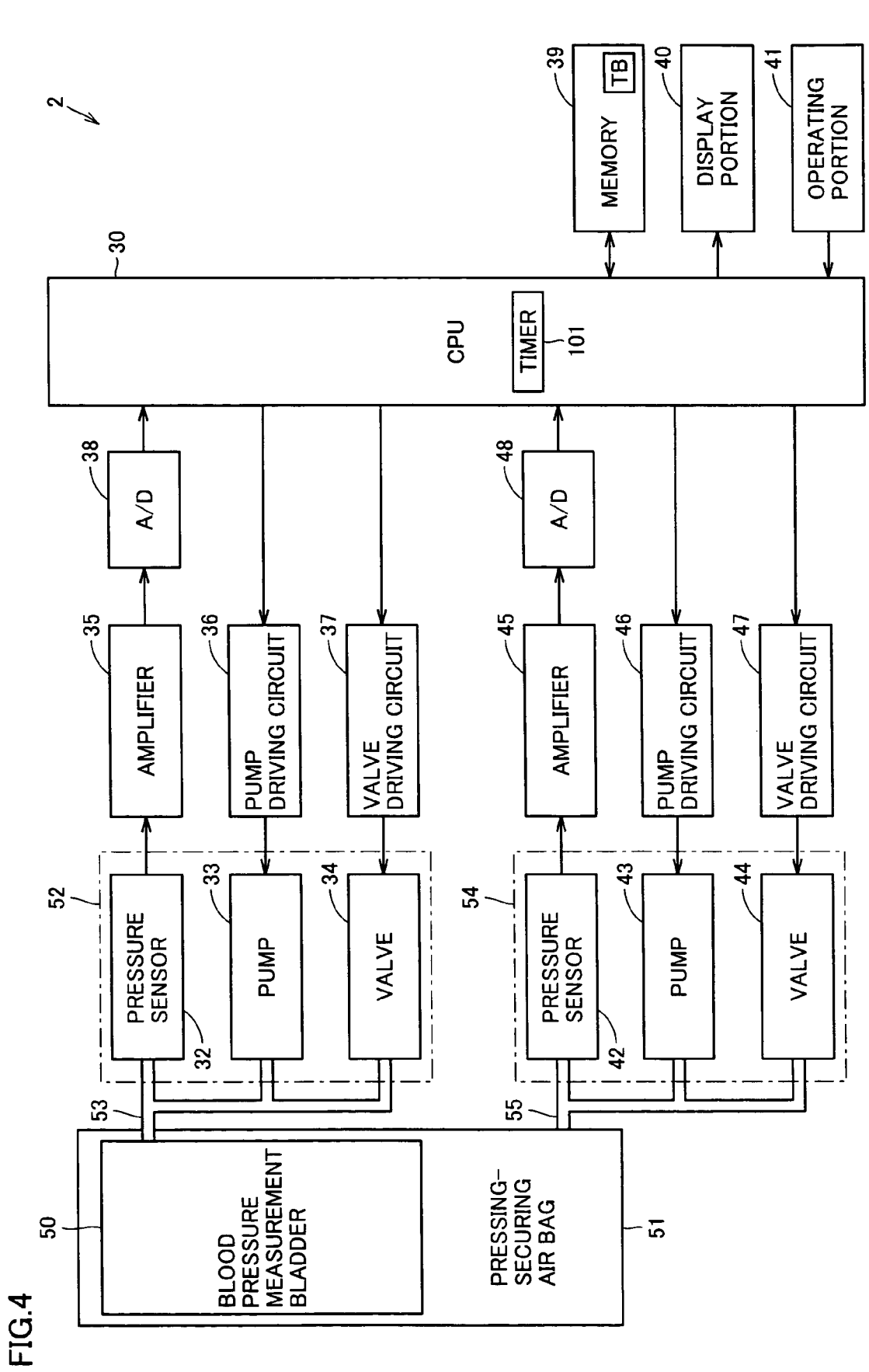
FIG. 4 is a block diagram of the automatically-wrapping type electronic blood pressure measurement device applied to an embodiment of the present invention.
Figure 5:
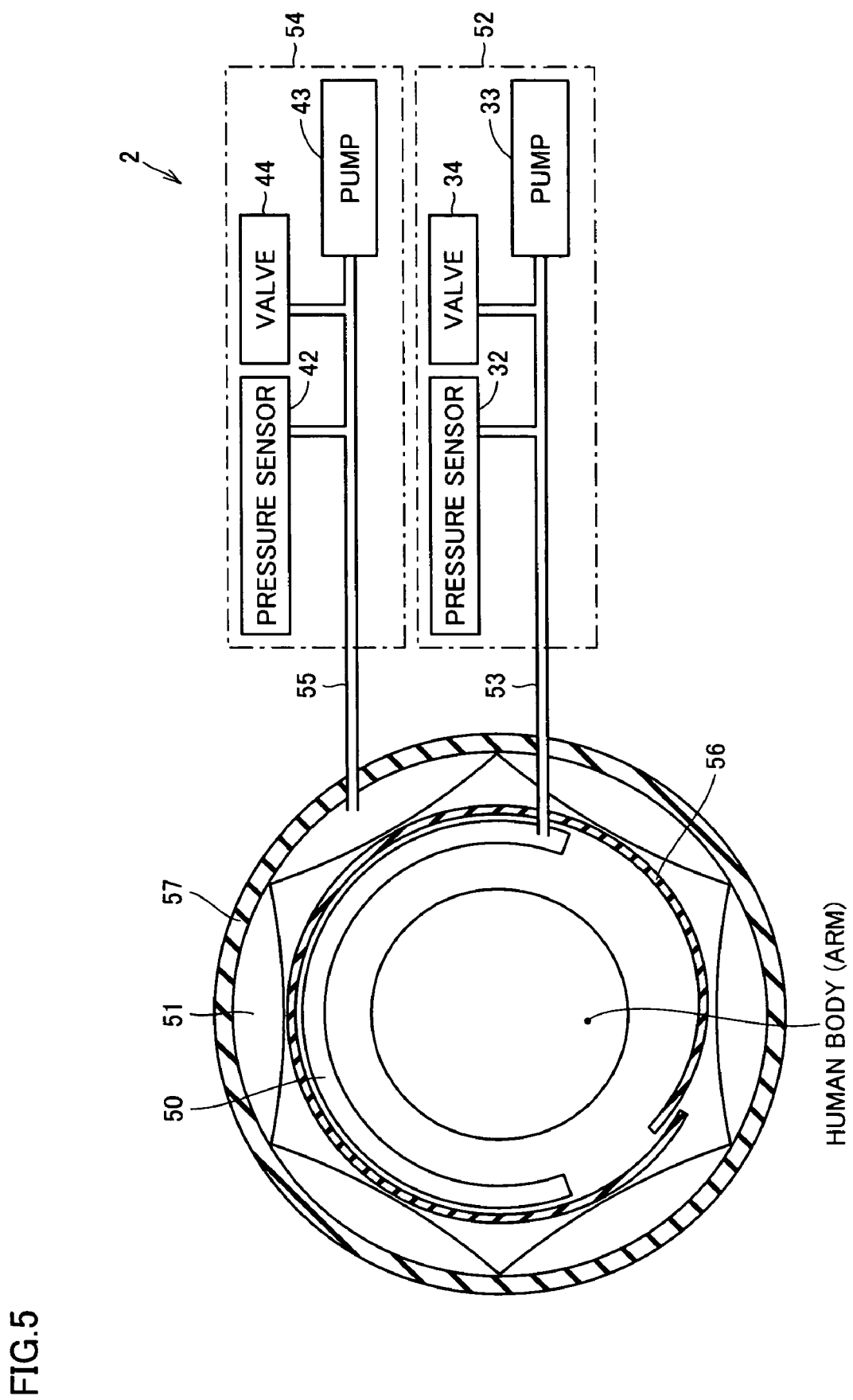
FIG. 5 shows a view illustrating an air system for the automatically-wrapping type electronic blood pressure measurement device.
Figure 6A:
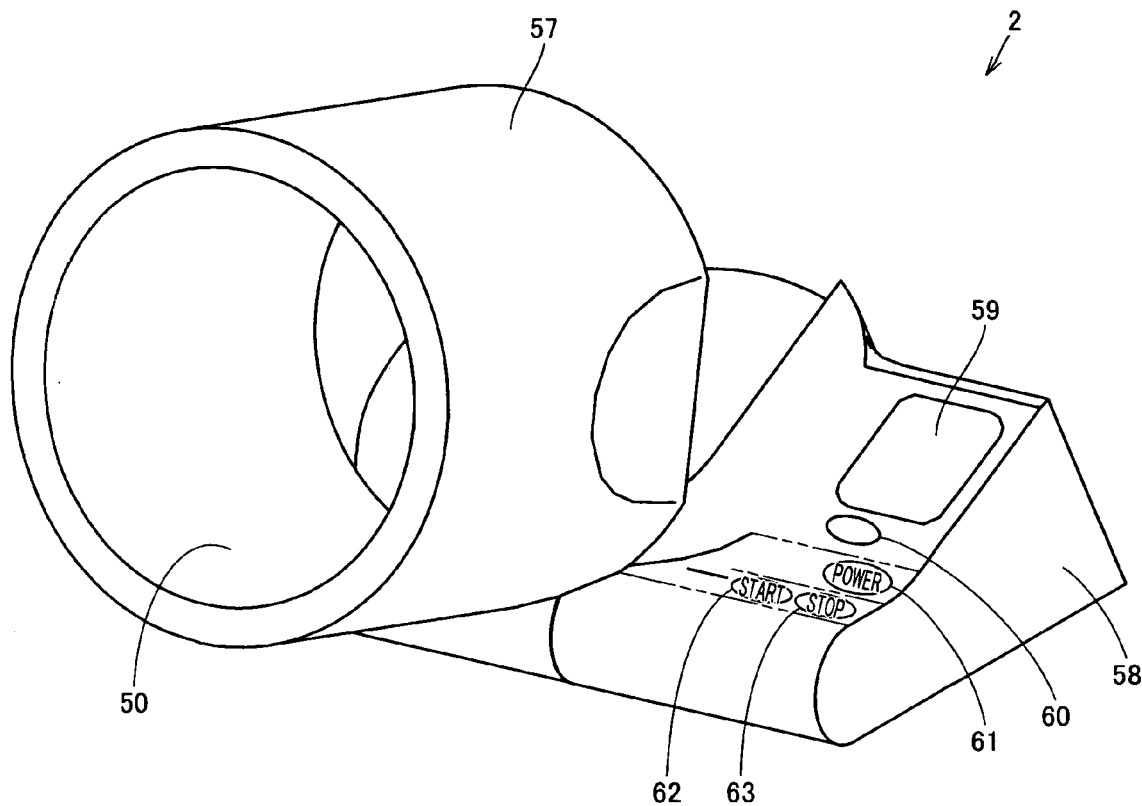
FIG. 6A and FIG. 6B show view schematically illustrating the outward appearance and the used state, respectively, of the automatically-wrapping type electronic blood pressure measurement device.
Figure 6B:
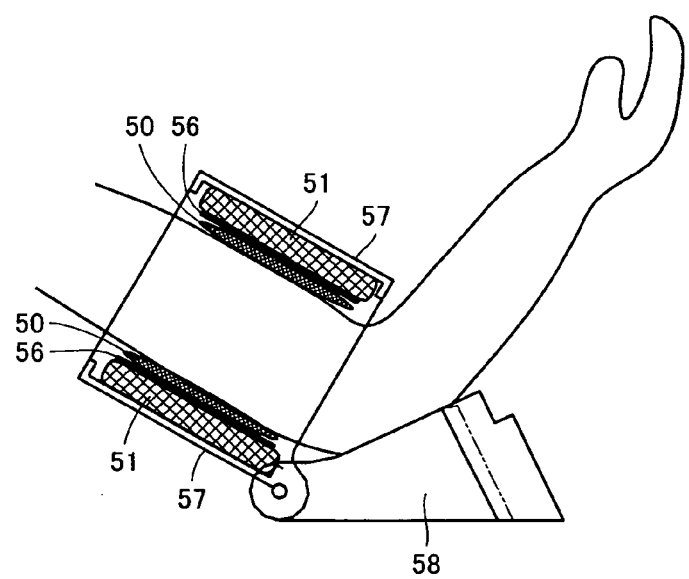

FIG. 1 illustrates a flowchart of blood pressure measurement which is common to the manually-wrapping type and automatically-wrapping type electronic blood pressure measurement devices according to the present embodiment of the present invention. FIG. 2 illustrates block structure of the manually-wrapping type electronic blood pressure measurement device applied to the present embodiment of the present invention and FIG. 3 illustrates the outward appearance of the manually-wrapping type electronic blood pressure measurement device. FIG. 4 illustrates the block structure of the automatically-wrapping type electronic blood pressure measurement device applied to the present embodiment of the present invention, FIG. 5 illustrates an air system of the automatically-wrapping type electronic blood pressure measurement device, and FIG. 6A and FIG. 6B schematically illustrate the outward appearance and the used state of the automatically-wrapping type electronic blood pressure measurement device.

(Device Configuration)

Referring to FIG. 2, a manually-wrapping type electronic blood pressure measurement device 1 includes a cuff 11 (blood pressure measurement bladder) enclosed within an arm cuff 23, which will be described later, to be mounted around the region for measurement of the subject, a pressure sensor 12 for detecting the pressure within cuff 11 (hereinafter, referred to as a cuff pressure) and outputting detection signals, a pump 13 and a valve 14 for controlling the pressure within cuff 11, an amplifier 15 for amplifying the output signals from pressure sensor 12, a pump driving circuit 16 for controlling the driving of pump 13, a valve driving circuit 17 for controlling opening and closing of valve 14, an A/D (analog/digital) converter 18 for converting analog signals output from amplifier 15 into digital signals and outputting the digital signals, a memory 19 for storing various information including measured blood pressure values, a display portion 20 for displaying various information such as measured blood pressure values, an operating portion 21 which is operated from the outside for inputting commands such as ON/OFF of the power supply of electronic blood pressure measurement device 1 and the start of measurement, and a CPU (Central Processing Unit) 10 for controlling the respective sections. CPU 10 includes a timer 101 for measuring the current time and memory 19 stores a table TB which will be described later.

Referring to FIG. 3, manually-wrapping type electronic blood pressure measurement device 1 further includes an arm cuff 23 adapted to be wrapped around the arm through a manual wrapping operation, and a main portion which is coupled to arm cuff 23 through a rubber tube 22. The main portion includes a lamp 25 and an LCD (Liquid Crystal Display) 26 as display portion 20 and further includes a power supply switch 27 and a pressurization switch 28 which is operated for starting a blood pressure measurement, as operating portion 21. Arm cuff 23 includes cuff 11 constituted by a rubber bag or a vinyl bag, a cloth belt enclosing cuff 11 and a ring 24 attached to one end of the belt for passing an end portion therethrough.

In wrapping arm cuff 23 around the region for measurement, the subject folds back the other end of the belt passed through ring 24 and removably secures it to the outer surface of the belt through a removable tape which is not shown. Thus, the subject can wrap arm cuff 23 around the arm by wrapping it along the outer surface of the belt by holding the other end thereof while passing his arm through the cylinder formed by the belt when the other end of the belt of arm cuff 23 has been passed through ring 24.

It is assumed that, in an appropriate wrapping determination process which will be described later, arm cuff 23 is manually and gradually wrapped around the arm while pump 13 is maintained at a stop.

Referring to FIG. 4 and FIG. 5, an automatically-wrapping type electronic blood pressure measurement device 2 includes a blood-pressure measurement bladder 50, a pressing-securing air bag 51 for pressing blood pressure measurement bladder 50 and securing it around the region for measurement, a blood pressure measurement air system 52 for supplying or discharging air to or from blood pressure measurement bladder 50 through a tube 53, an amplifier 35, a pump driving circuit 36, a valve driving circuit 37 and an A/D converter 38 provided in relation to blood pressure measurement air system 52. Further, automatically-wrapping type electronic blood pressure measurement device 2 includes a pressing-securing air system 54 for supplying or discharging air to or from pressing-securing air bag 51 through a tube 55, an amplifier 45, a pump driving circuit 46, a valve driving circuit 47 and an A/D converter 48 provided in relation to pressing-securing air system 54. Automatically-wrapping type electronic blood pressure measurement device 2 further includes a CPU 30 for centrally controlling and monitoring the respective sections, a memory 39 for storing various information such as measured blood pressure values, display portion 40 for displaying various information including the results of blood pressure measurements, and an operating portion 41 which is operated for inputting various commands for measurements.

Blood pressure measurement air system 52 includes a pressure sensor 32 for detecting and outputting the pressure in blood pressure measurement bladder 50 (hereinafter, referred to as a cuff pressure), a pump 33 for supplying air to blood pressure measurement bladder 50, and a valve 34 which is opened or closed in order to discharge or enclose air from or into blood pressure measurement bladder 50. Amplifier 35 amplifies output signals from pressure sensor 32 and outputs them to A/D converter 38, and A/D converter 38 converts the output analog signals into digital signals and outputs the converted signals to CPU 30. Pump driving circuit 36 controls the driving of pump 33 based on control signals from CPU 30. Valve driving circuit 37 executes the opening/closing control for valve 34 based on control signals from CPU 30.

Pressing-securing air system 54 includes a pressure sensor 42 for detecting and outputting the pressure in pressing-securing air bag 51, a pump 43 for supplying air to pressing-securing air bag 51, and a valve 44 which is opened or closed in order to discharge or enclose air from or into pressing-securing air bag 51. Amplifier 45 amplifies output signals from pressure sensor 42 and outputs them to A/D converter 48, and A/D converter 48 converts the output analog signals into digital signals and outputs the converted signals to CPU 30. Pump driving circuit 46 controls the driving of pump 43 based on control signals from CPU 30. Valve driving circuit 47 executes opening/closing control for valve 44 based on control signals from CPU 30.

Referring to FIG. 6A, automatically-wrapping type electronic blood pressure measurement device 2 includes a securing cylindrical case 57 for securing the arm, which is the region for measurement, of the subject and a blood-pressure measurement device main portion 58. Blood-pressure measurement device main portion 58 includes an LCD 59 and a lamp 60 as display portion 40. Blood-pressure measurement device main portion 58 further includes a power-supply switch 61, a start switch 62 and a stop switch 63 for dictating the start and the stop of a blood pressure measurement, as operating portion 41, in order to enable external operation. Securing cylindrical case 57 includes, on its inner surface, blood-pressure measurement bladder 50 to be mounted around the region for measurement. In FIG. 6B, there is illustrated a state where the arm, which is the region for measurement, of the subject is inserted through securing cylindrical case 57 from the front side thereof in the figure, in order to measure the blood pressure.

FIG. 5 schematically illustrates a cross sectional view of securing cylindrical case 57 at the state illustrated in FIG. 6B. Securing cylindrical case 57 is provided with measurement bladder 50, a pressing-securing curled elastic member 56, the size of which in a radial direction is expansible, and pressing-securing air bag 51, from the outer circumference of the arm which is the region for measurement toward the inner surface of securing cylindrical case 57. When pressing-securing air bag 51 is inflated by supplying air thereto through pressing-securing air system 54, the size of pressing-securing curled elastic member 56 in a radial direction is decreased by the effect thereof. Thus, in association with this, measurement bladder 50 interposed between pressing-securing curled elastic member 56 and the human body (arm) is pressed against the region for measurement. Thus, measurement bladder 50 is wrapped and secured around the human body (arm) through pressing-securing curled elastic member 56 and pressing-securing air bag 51, thereby enabling blood-pressure measurements.

It is assumed that, in the appropriate wrapping determination process which will be described later, pump 43 is driven while pump 33 is maintained at a stop, and thus pressing-securing air bag 51 is gradually supplied with air to be inflated, thereby causing measurement bladder 50 to be automatically wrapped around the arm.

(Blood Pressure Measurement Process)

There will be described, according to FIG. 1, the general outlines of the blood pressure measurement process using manually-wrapping type electronic blood pressure measurement device 1 or automatically-wrapping type electronic blood pressure measurement device 2.

A program according to the flowchart of FIG. 1 is stored in an internal memory, which is not shown, in CPU 10 or 30 and read out therefrom and executed under the control of CPU 10 or 30.

When the power supply is turned on at first and switch 28 or 62 is operated, CPU 10 or 30 initializes the blood pressure measurement device. Thus, the cuff pressure in cuff 11 or blood pressure measurement bladder 50 or the internal pressure in pressing-securing air bag 51 is initialized to, for example, an atmospheric pressure (step ST1). Then, pre-pressurization is performed (step ST2). Namely, CPU 10 or 30 closes valve 34 or valve 14 for blood pressure measurement bladder 50 or cuff 11 and then supplies, thereto through pump 33 or pump 13, a predetermined amount of air which causes the cuff pressure to be within a pressure-level range which enables the appropriate wrapping determination, which will be described later. Then CPU 10 or 30 stops pump 33 or pump 13. Data of the pressure level is prestored in a memory in the CPU. The amount of air to be supplied thereto is small and has been empirically determined in advance. This amount will vary depending on the size of cuff 11 or blood pressure measurement bladder 50. Then, CPU 10 causes lamp 25 to light up in a color giving instruction of "Please, wrap", for example, in a green color (step ST3). In the case of automatically-wrapping type electronic blood pressure measurement device 2, valve 44 is closed and pressing-securing air bag 51 is supplied with air through pump 43, thus starting the wrapping of blood pressure measurement bladder 50.

Then, a process for determining whether or not measurement bladder 50 or cuff 11 has been wrapped around the region for measurement with a proper pressure for blood pressure measurements regardless of the length around the arm which is the region for measurement (hereinafter, referred to as an appropriate wrapping determination process) is executed (step ST4). When it is determined in the appropriate wrapping determination process that blood pressure measurement bladder 50 or cuff 11 has been properly wrapped around the region for measurement of the subject, CPU 10 causes lamp 25 to light up in a red color and instructs, through the lighting thereof, the subject to cease the operation of wrapping arm cuff 23 (step ST5). In the case of automatically-wrapping type electronic blood pressure measurement device 2, pump 43 is stopped to terminate the wrapping of blood pressure measurement bladder 50.

While the instructions in steps ST3 and ST5 are given using lamp 25 herein, a buzzer which is not shown may be provided and the instructions may be given through the buzzer. Also, such instructions may be displayed on LCD 26.

Then, it is determined whether or not the wrapping of the arm cuff has been ceased (stop ST6). In the case of an automatically-wrapping type electronic blood pressure measurement device 2, the determination is performed based on whether or not pump 43 has been stopped, while in the case of manually-wrapping type electronic blood pressure measurement device 1 the determination is performed based on whether or not the cuff pressure indicated by output signals from pressure sensor 12 is maintained constant for a predetermined time period. If the result of the determination reveals that the wrapping has not been ceased (N in step ST6), a predetermined error process (step ST12) is executed and the blood pressure measurement is terminated. On the other hand, if the result of the determination reveals that the wrapping has been ceased (Y in step ST6), the process proceeds to subsequent blood pressure measurement processes.

In measuring the blood pressure, at first, pump 13 or pump 33 is driven to supply air to cuff 11 or blood pressure measurement bladder 50, thereby gradually raising the cuff pressure. When it is determined, based on output signals from pressure sensor 12 or 32, that the cuff pressure has reached a predetermined level indicated by data prestored in a memory, which is not shown, in the CPU (step ST7), CPU 10 or 30 controls valve 14 or valve 34 such that it is gradually opened to cause slow discharge, thus gradually reducing the cuff pressure (step ST8). In parallel with the depressurization process, CPU 10 or 30 calculates the values of blood pressures (systolic blood pressure and diastolic blood pressure), based on pulse pressure signals superimposed on signals detected by pressure sensor 12 or pressure sensor 32, according to a predetermined process (step ST9). The blood pressure calculation process is well known and is not described herein. The obtained blood pressure values are displayed on display device 20 or 40 (step ST10). Subsequently, CPU 10 or 30 controls valve 14 or valve 34 and valve 44 such that they are fully opened to discharge air from cuff 11 or blood pressure measurement bladder 50 and pressing-securing air bag 51 (step ST11). Thus, the blood pressure measurement process is completed.

(Appropriate Wrapping Determination Process)

Next, processes in the appropriate wrapping determination process in FIG. 1 (step ST4) will be described. In the present embodiment, any of the following first to fourth exemplary determinations may be employed as the process. The first to fourth exemplary determinations may be similarly applied to manually-wrapping type electronic blood pressure measurement device 1 and automatically wrapping type electronic blood pressure measurement device 2.

(First Exemplary Determination)

In the first exemplary determination according to the process of FIG. 7, in focusing attention on the fact that the cuff pressure varies depending on the length around the arm (hereinafter, referred to as an arm circumferential length L) after the completion of pre-pressurization, the appropriate wrapping determination is performed based on the relative difference between the cuff pressure just after the completion of pre-pressurization and the cuff pressure detected during the manual wrapping or the inflation of pressing-securing air bag 51 after the completion of pre-pressurization. Therefore, a determination threshold value FIT1 indicative of a relative difference for use in the appropriate wrapping determination is set to be constant, regardless of the value of arm circumferential length L.

Figure 8:
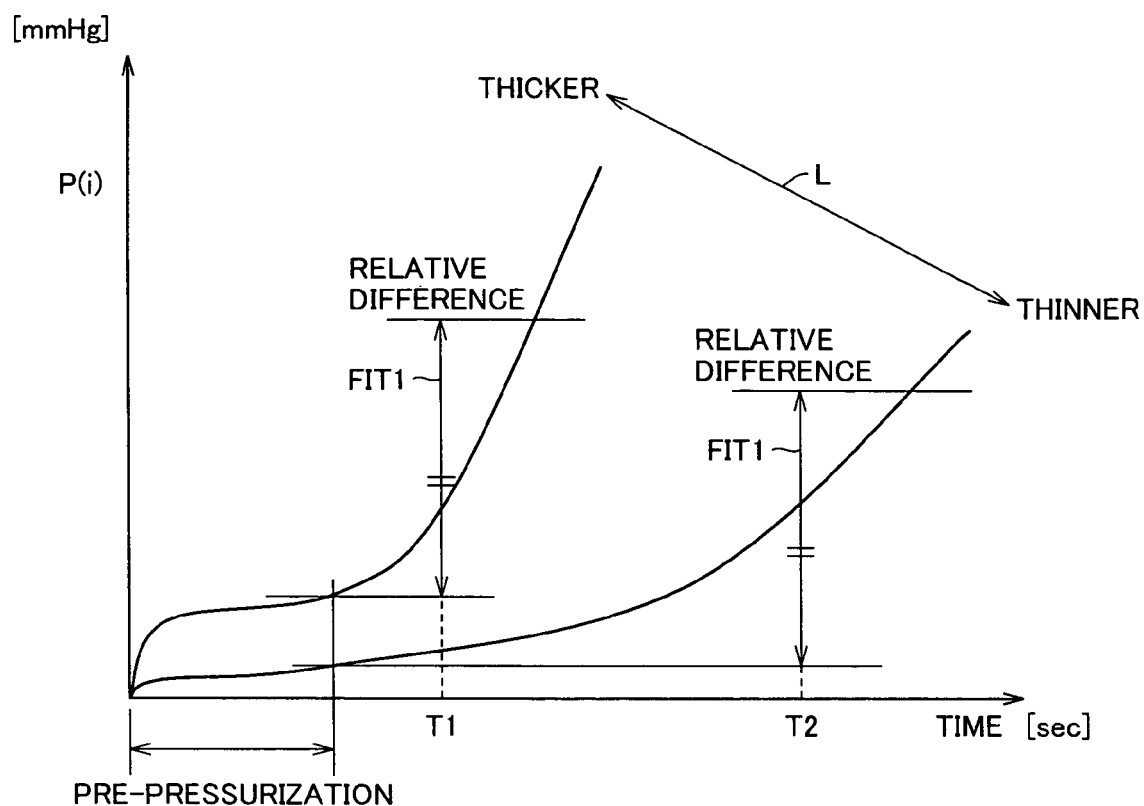
FIG. 8 shows a view for describing the first exemplary determination.

FIG. 8 illustrates, for describing the first exemplary determination, the variation in the measurement bladder pressure P(i) (cuff pressure) with time. The subscript character "i" of measurement bladder pressure P(i) designates the counting value of the number of samplings, in order to acquire the cuff pressure by sampling. The sampling period, which is measured by timer 101, is 5.12 msec, for example. FIG. 8 illustrates, with a curve, the variation in the value of measurement bladder pressure P(i) with time. As can be seen from FIG. 8, in the case where the arm is thicker (the value of the arm circumferential length L is larger), the cuff pressure has been sufficiently raised already at the completion of the pre-pressurization by the pressure caused by the arm itself, and therefore the relative difference reaches the determination threshold value FIT1 with an early timing T1, when the wrapping is started after the completion of pre-pressurization. On the contrary, in the case where the arm is thinner (the value of the arm circumferential length L is smaller), the relative difference reaches the determination threshold value FIT1 with a timing T2 later than timing T1.

Figure 7:
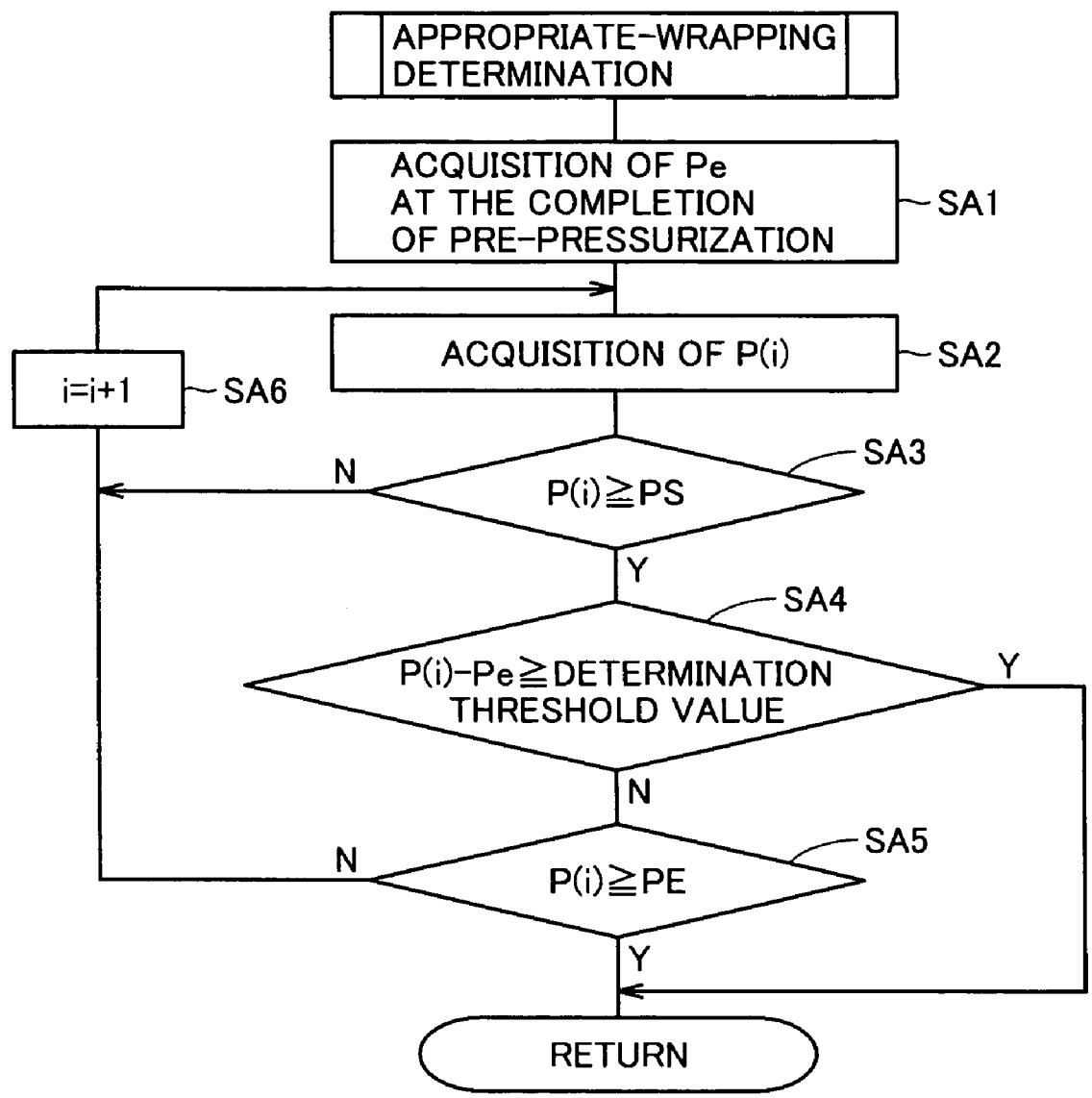
FIG. 7 is a flowchart of a first exemplary determination.

In the process of FIG. 7, first, at the completion of pre-pressurization, CPU 10 or 30 acquires (detects) the measurement bladder pressure Pe, which is the cuff pressure, based on output signals from pressure sensor 12 or 32, (step SA1). Then, in the case of manually-wrapping type electronic blood pressure measurement device 1, the subject gradually wraps an end portion of the belt enclosing cuff 11 around the arm. Also, in the case of automatically-wrapping type electronic blood pressure measurement device 2, CPU 30 drives pump 43 to gradually supply air to pressing-securing air bag 51, thus gradually wrapping measurement bladder 50 around the arm through curled elastic member 56.

In the wrapping process, CPU 10 or 30 acquires (detects) the measurement bladder pressure P(i), which is the cuff pressure (step SA2) and then determines whether or not the value of the acquired measurement bladder pressure P(i) has reached the value of a predetermined determination start pressure PS, which has been prestored (step SA3). The predetermined determination start pressure PS corresponds to a level (which has been empirically determined in advance) sufficiently lower then pressure levels at appropriate wrapping states. If it has not reached the determination start pressure PS (N in step SA3), a next measurement bladder pressure P(i) is determined (steps SA6 and SA2). On the other hand, if measurement bladder pressure P(i) has reached the determination start pressure PS (Y in step SA3), CPU 10 or 30 determines whether or not the relative difference between measurement bladder pressure Pe acquired at the completion of pre-pressurization and the current measurement bladder pressure P(i) is above the predetermined determination threshold value FIT1 (for example, 20 mmHg) which has been prestored (step SA4). If it is above the predetermined determination threshold value FIT1 (Y in step SA4), it is determined that the appropriate wrapping state has been achieved and then the process proceeds to the next process (step ST5). At this time, in the case of automatically-wrapping type electronic blood pressure measurement device 2, pump 43, which has been driven for blood pressure measurement bladder 50, is stopped.

If the relative difference is below the determination threshold value FIT1 (N in step SA4), it is determined whether or not the current measurement bladder pressure P(i) is above a determination termination pressure PE required for terminating the appropriate wrapping determination, namely a prestored predetermined pressure level required for starting blood pressure measurements (step SA5). As a result of the determination, if the current measurement bladder pressure P(i) has not reached the predetermined determination termination pressure PE, a next measurement bladder pressure P(i) is determined (steps SA6 and SA2) and the subsequent processes are repeated. On the other hand, if it has reached, it is determined that the appropriate wrapping state has been achieved and thus the process proceeds to the next process (step ST5). At this time, in the case of automatically-wrapping type electronic blood pressure measurement device 2, pump 43, which has been driven for wrapping measurement bladder 50, is stopped.

The aforementioned process in step SA5 is provided in consideration of the fact that, in the case where the arm is extremely thick, the measurement bladder pressure P(i) reaches the pressure required for starting a blood pressure measurement before the relative difference reaches the determination threshold value FIT1.

(Second Exemplary Determination)

Figure 9:
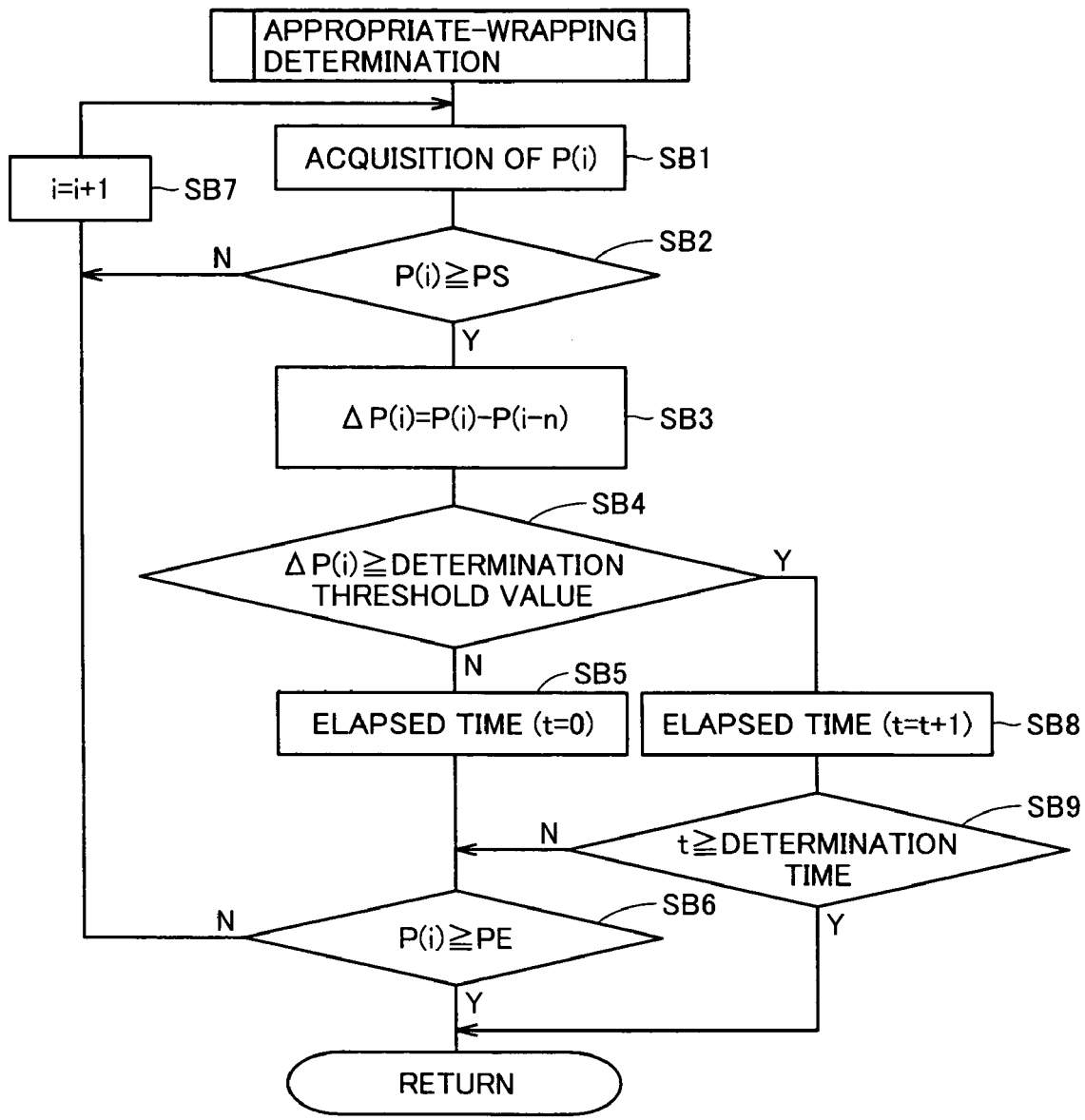
FIG. 9 is a flowchart of a second exemplary determination.
Figure 10:
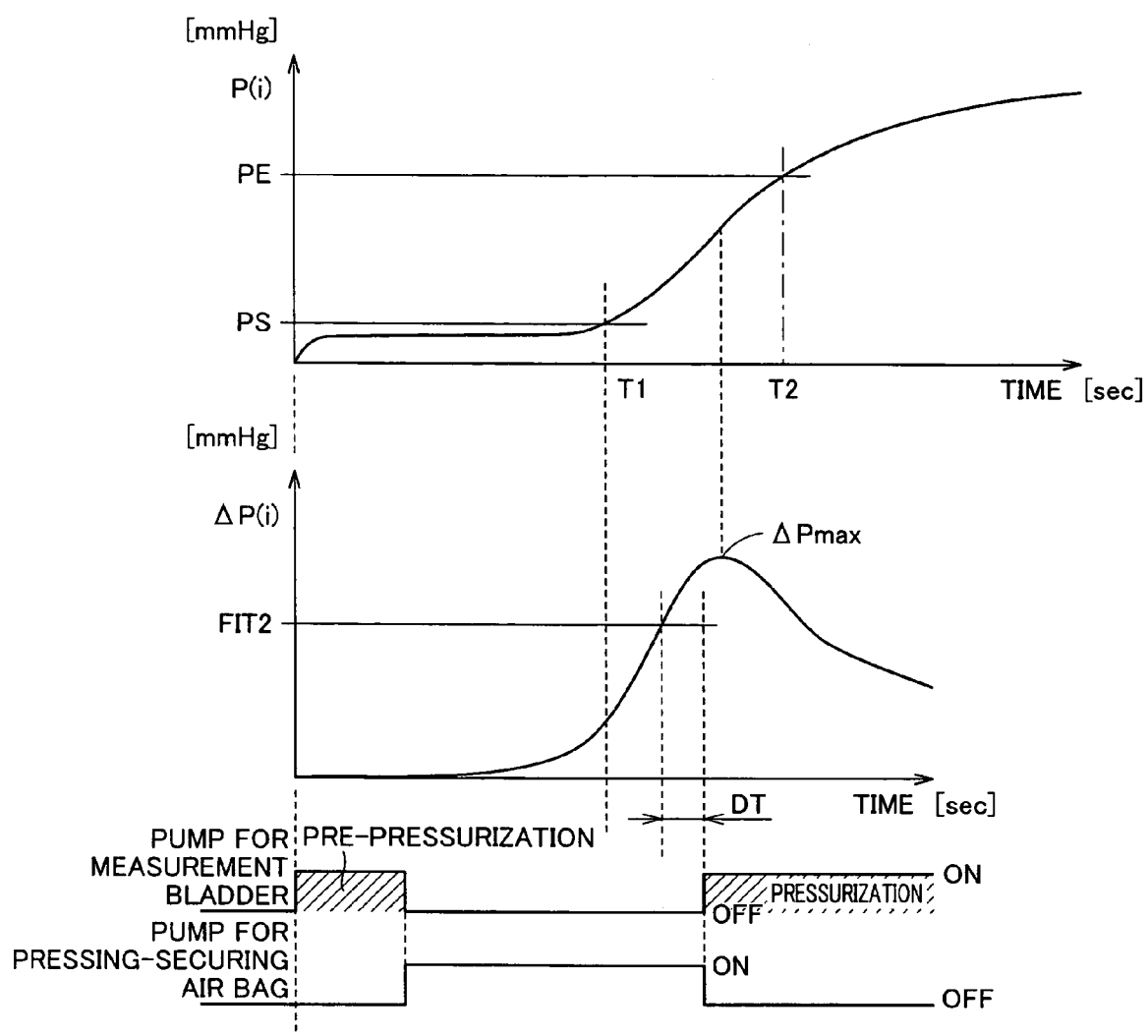
FIG. 10 shows a view for describing the second exemplary determination.
Figure 11:
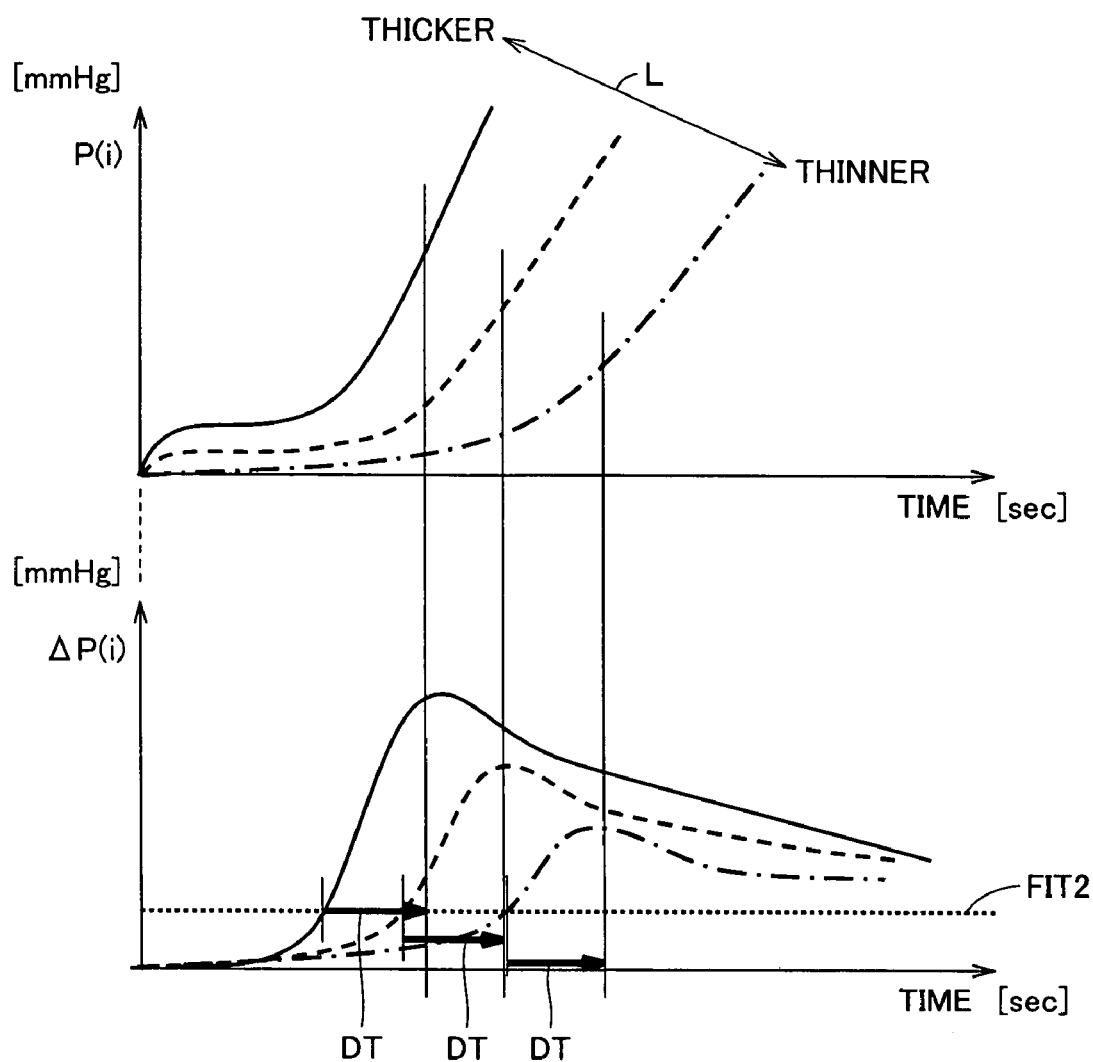
FIG. 11 shows a view for describing the second exemplary determination.

In the second exemplary determination, appropriate wrapping detection is performed based on relative variations in the cuff pressure during the raising process thereof FIG. 9 illustrates the process thereof and FIG. 10 and FIG. 11 illustrate the variation in the measurement bladder pressure P(i) with time and the variation in the measurement bladder pressure variation ΔP(i) with time. In FIG. 10, there are illustrated the operation (ON) and the stop (OFF) of pump 33 and pump 43 in relation to the aforementioned variations.

Referring to FIG. 9, CPU 10 or 30 acquires (detects) the measurement bladder pressure P(i) through pressure sensor 12 or 32, after the completion of pre-pressurization (step SB1).

It is determined whether or not the acquired measurement bladder pressure P(i) has reached a predetermined determination starting pressure PS which has been prestored (see FIG. 10) (step SB2). If it has not reached (N in step SB2), the process returns to step SB1 through the process in step SB7 in order to newly acquire the measurement bladder pressure P(i). On the other hand, if it has reached the predetermined determination starting pressure PS (see a timing T1 in FIG. 10), the measurement bladder pressure variation ΔP(i) is determined based on the equation: (P(i)–P(i–n)) (step SB3). At this time, the measurement bladder pressure P(i) is acquired once every 5.12 msec, for example, and the value of the variable n in the aforementioned equation is, for example, 3.

It is determined whether or not the determined measurement bladder pressure variation ΔP(i), which is a relative change, has reached a prestored determination threshold value FIT2 illustrated in FIG. 10. Even when it has reached, the variation ΔP(i) may have merely reached the determination threshold value FIT2 due to temporary noise. Therefore, the duration of time it reaches the determination threshold value FIT2 is measured using a counter t and it is monitored, based on the value of counter t, whether or not the condition where it reaches the determination threshold value FIT2 continues for a prestored predetermined determination time DT illustrated in FIG. 10 (steps SB8 and SB9). If it has continued (Y in step SB9), it is determined that appropriate wrapping is achieved and the process ends. In the case of automatically-wrapping type electronic blood pressure measurement device 2, pump 43 which has been driven for wrapping measurement bladder 50 is stopped, at the completion of the determination process.

On the other hand, if the measurement bladder pressure variation ΔP(i) has not reached the determination threshold value FIT2 (N in step SB4), the value of counter t is set to 0 (step SB5) and it is determined whether or not the measurement bladder pressure P(i) has reached the prestored determination termination pressure PE illustrated in FIG. 10 (step SB6). If it has reached, a appropriate wrapping state has been achieved and therefore the process ends. Further, when it is determined in step SB9 that the condition has not continued for the determination time DT, it is determined whether or not the measurement bladder pressure P(i) has reached the determination termination pressure PE (step SB6). If it has not reached (N in step SB6), the process proceeds to a step SB7 and then a next measurement bladder pressure P(i) is acquired (step SB1). If it has reached (see a timing T2 in FIG. 10), the appropriate wrapping state has been achieved and therefore the process ends.

With reference to FIG. 11, there will be described the relationship between the arm circumferential length L and the variation in the measurement bladder pressure P(i) during the raising process thereof, in relation to the second exemplary determination. As illustrated in the upper area in FIG. 11, the variation in the measurement bladder pressure P(i) with time varies depending on the value of arm circumferential length L designated by an arrow. In association with this, the variation in the measurement bladder pressure variation ΔP(i) varies depending on the value of arm circumferential length L, as illustrated in the lower area in FIG. 11. Therefore, by using the measurement bladder pressure variation ΔP(i), appropriate wrapping determination can be performed regardless of the value of arm circumferential length L.

(Third Exemplary Determination)

Figure 12:
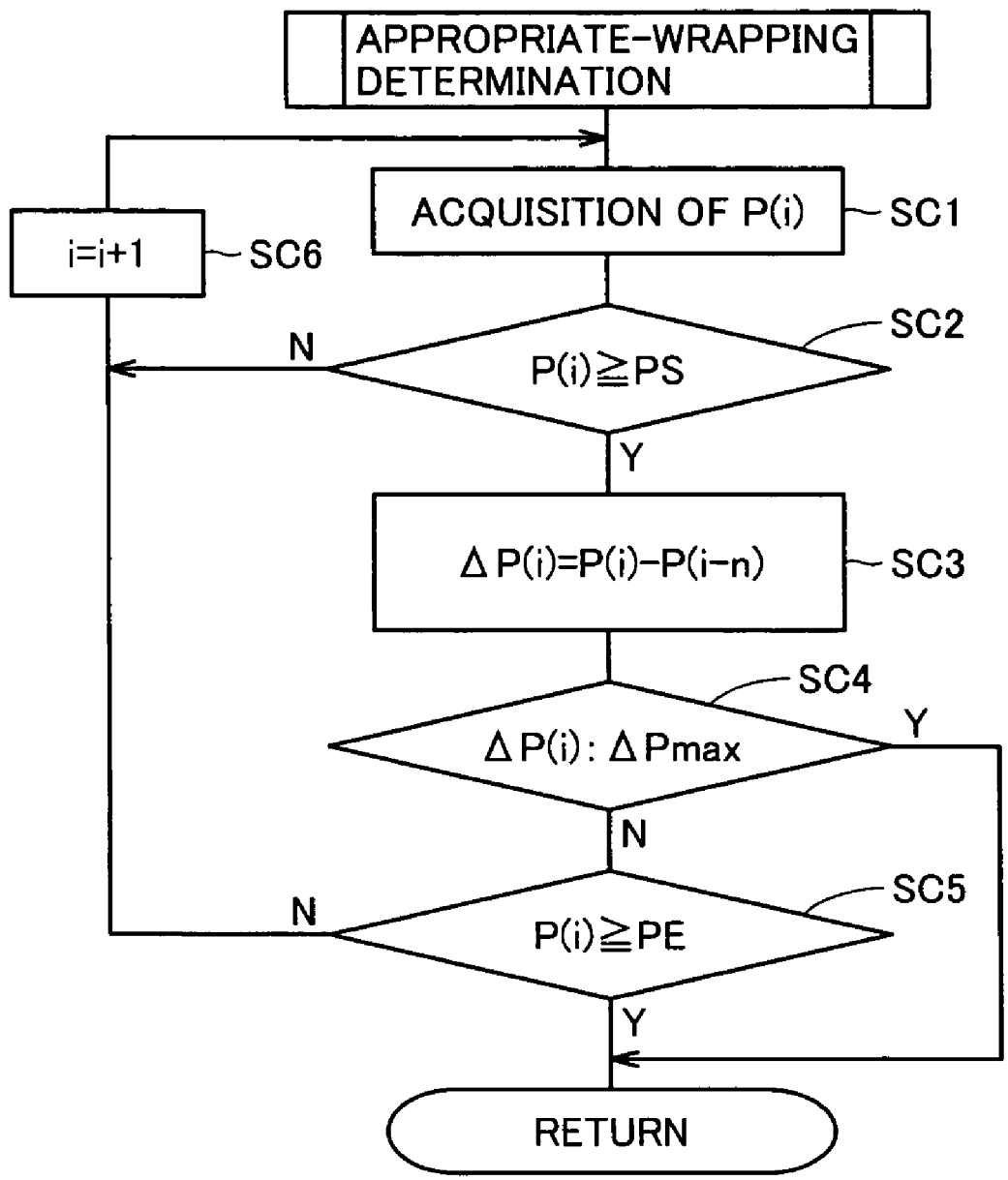
FIG. 12 is a flowchart of a third exemplary determination.
Figure 13:
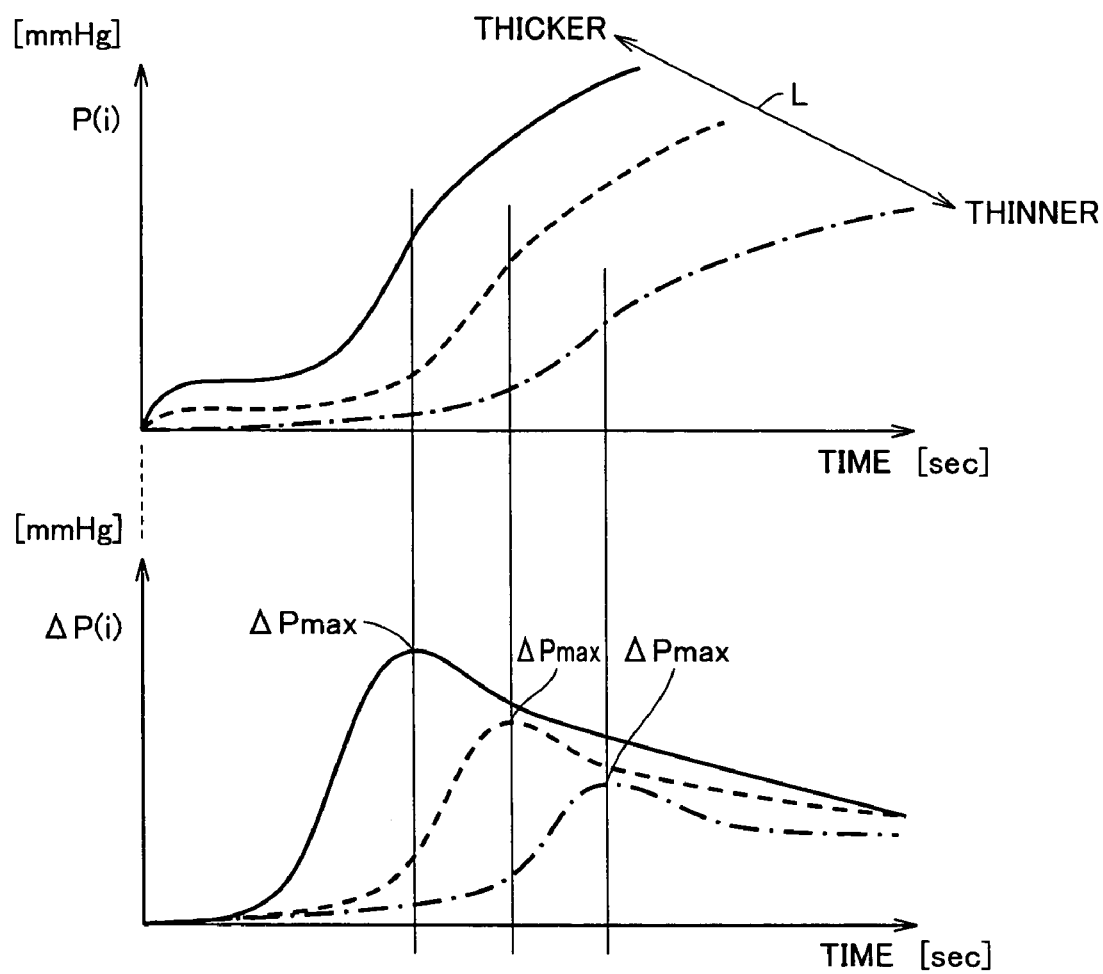
FIG. 13 shows a view for describing the third exemplary determination.

With reference to FIG. 13, third exemplary determination will be described according to a flowchart of FIG. 12.

With reference to FIG. 13, there will be described the arm circumferential length L designated by an arrow and the variation in measurement bladder pressure P(i) during the raising process thereof. As illustrated in the upper area in FIG. 13, the variation in measurement bladder pressure P(i) with time varies depending on the value of arm circumferential length L. In association with this, the variation in the measurement bladder pressure variation ΔP(i) varies depending on the value of arm circumferential length L, as illustrated in the lower area. Further, the peak value (maximum value) ΔPmax of measurement bladder pressure variation ΔP(i) also varies depending on the value of arm circumferential length L. When measurement bladder pressure variation ΔP(i) reaches a peak value ΔPmax, cuff 11 or blood pressure measurement bladder 50 has been properly brought into intimate contact with the region for measurement, namely into the appropriate wrapping state, after the start of wrapping. If the wrapping is further advanced from this state, the region for measurement will be squeezed, thus degrading the accuracy of subsequent blood pressure measurements or inflicting pain on the subject.

In the present exemplary determination, as illustrated in FIG. 13, when the time measurement bladder pressure variation ΔP(i) reaches a peak value ΔPmax, it is determined that appropriate wrapping has been achieved, in focusing attention on the fact that the peak value (maximum value) ΔPmax varies depending on the value of arm circumferential length L, Thus, appropriate wrapping states can be accurately detected regardless of the value of arm circumferential length L.

Referring to FIG. 12, CPU 10 or 30 acquires measurement bladder pressure P(i) after the completion of pre-pressurization (step SC1) and then determines whether or not the acquired measurement bladder pressure P(i) has reached the determination starting pressure PS (step SC2). If it has not reached determination starting pressure PS, the process returns to step SC1 through the process in step SC6 in order to determine the next measurement bladder pressure. If it has reached determination starting pressure PS, a measurement bladder pressure variation ΔP(i) is determined similarly to in the second exemplary determination (step SC3). Then, it is determined whether or not the determined measurement bladder pressure variation ΔP(i) has reached a peak value ΔPmax (step SC4). When it has reached a peak value ΔPmax, it is determined that appropriate wrapping has been achieved (Y in step SC4), and the appropriate wrapping determination process ends. At the completion of the determination, in the case of automatically-wrapping type electronic blood pressure measurement device 2, pump 43, which has been driven for wrapping measurement bladder 50, is stopped.

On the other hand, when it has not reached a peak value ΔPmax, it is determined whether or not the measurement bladder pressure P(i) has reached a determination termination pressure PE (step SC5). When it has not reached (N in step SC5), the process proceeds to the process in step SC6, then the next measurement bladder pressure P(i) is determined, again (step SC1) and then the subsequent processes are repeated. When it has reached, it is determined that appropriate wrapping has been achieved and the appropriate wrapping determination process ends.

For example, it can be determined, from the following process, that the measurement bladder pressure variation ΔP(i) has reached a peak value ΔPmax. Namely, during raising the measurement bladder pressure P(i), each time a measurement bladder pressure variation ΔP(i) is calculated in step SC3, the current calculated measurement bladder pressure variation ΔP(i) is compared with the previously-calculated measurement bladder pressure variation ΔP(i). When the result of the comparison indicates that the current calculated measurement bladder pressure variation ΔP(i) is smaller than the previously-calculated measurement bladder pressure variation ΔP(i), CPU 10 or 30 can determines that the measurement bladder pressure variation ΔP(i) has reached a peak value ΔPmax. This process will be more apparently understood with reference to FIG. 13.

(Fourth Exemplary Determination)

Figure 14:
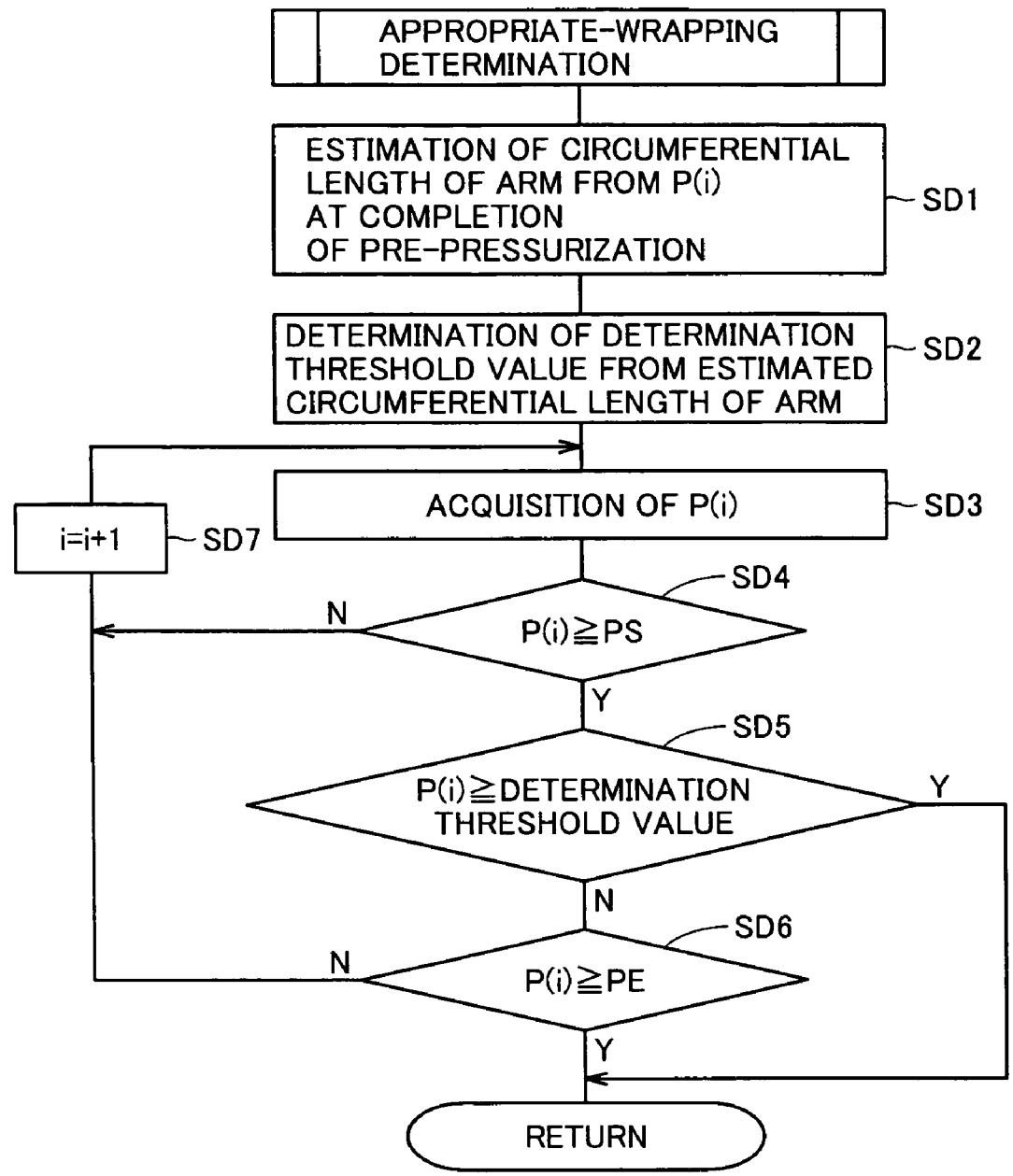
FIG. 14 is a flowchart of a fourth exemplary determination.
Figure 15:
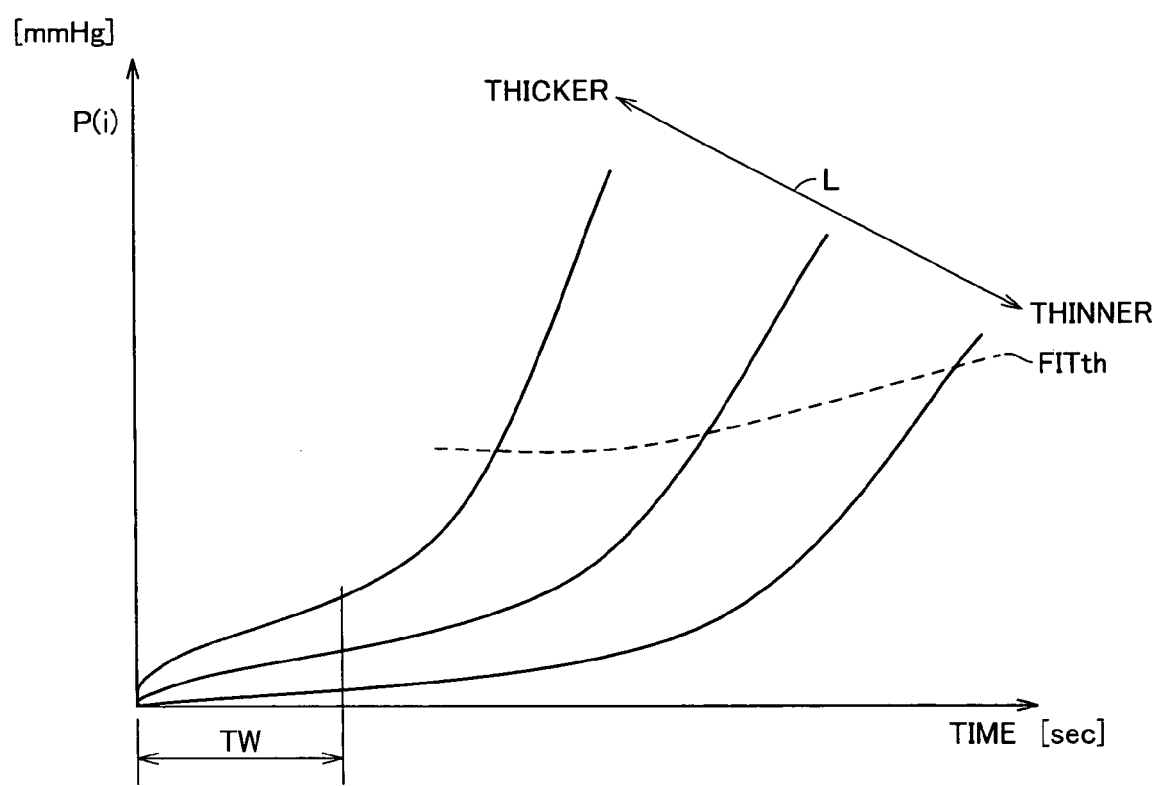
FIG. 15 shows a view for describing the fourth exemplary determination.

With reference to FIG. 14 and FIG. 15, a fourth exemplary appropriate wrapping determination will be described. While threshold values FIT1 and FIT2 are fixed values in the aforementioned first and second determination, these values may be altered depending on the arm circumferential length L as will be described in the fourth exemplary determination.

In FIG. 15, there is shown that the arm circumferential length L is estimated based on the variation (gradient) in the detected measurement bladder pressure P(i) (or the measurement bladder pressure variation ΔP(i)) at a predetermined arm circumferential length determination time TW since the appropriate wrapping determination process is entered after the completion of pre-pressurization. The estimation is performed as follows, for example. At first, variations and respective corresponding arm circumferential length values are determined in advance by experiments, and a table TB associating the respective variations with the corresponding values of arm circumferential length L and with determination threshold values is prestored in memory 19 or 39. Then, by retrieving table TB based on the variation detected at the arm circumferential length determination time TW since the start of the appropriate wrapping determination, the corresponding value of arm circumferential length L can be identified (estimated). At this time, the corresponding determination threshold value can be identified from table TB. By reading out both the identified values from table TB, it is possible to acquire the results of processes in steps SD1, SD2 which will be described later.

Also, the identification of the determination threshold value is not limited to the aforementioned method which searches table TB may be attained as follows. For example, the determination threshold value may be determined based on the equation (the determination threshold value=α×(arm circumferential length L)$^2$+β×(arm circumferential length L)+γ, wherein α, β and γ are arbitrary values).

Next, the appropriate wrapping determination process of the present exemplary determination will be described according to FIG. 14. At first, CPU 10 or 30 estimates the value of arm circumferential length L, based on the measurement bladder pressure P(i) acquired at predetermined arm circumferential length determination time TW after the completion of pre-pressurization, as previously described (step SD1) and determines the determination threshold value FITth based on the estimated value of arm circumferential length L (step SD2). The determined determination threshold value FITth is represented by a broken line in FIG. 15.

Next, measurement bladder pressure P(i) is acquired (detected) (step SD3) and it is determined whether or not the acquired measurement bladder pressure P(i) has reached a determination starting pressure PS (step SD4). If it has not reached determination starting pressure PS, the process returns to the process in step SD3 through a step SD7, in order to determine a next measurement bladder pressure P(i).

On the other hand, if it has reached determination starting pressure PS, it is determined whether or not the measurement bladder pressure P(i) has reached determination threshold value FITth for appropriate wrapping determination (step SD5). As a result of the determination, if it has reached determination threshold value FITth, the appropriate wrapping determination ends. At the completion of the determination process, in the case of automatically-wrapping type electronic blood pressure measurement device 2, pump 43 which has been driven for wrapping measurement bladder 50 is stopped. If it has not reached determination threshold value FITth, it is determined whether or not it has reached a determination termination pressure PE (step SD6). If it has not reached, the process returns to step SD3 through the process in step SD7 in order to acquire the next measurement bladder pressure P(i). On the other hand, if it has reached determination termination pressure PE, the appropriate wrapping determination ends.

The process for variably setting determination threshold value FITth based on the arm circumferential length L according to the present exemplary determination may be applied for the determination threshold values of the aforementioned first to third exemplary determinations to detect appropriate wrapping states more accurately. As a result, the accuracy of blood pressure measurements can be also improved.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A blood pressure measurement cuff wrapping control device for controlling wrapping of a blood pressure measurement cuff including a bladder, which is inflated when supplied with fluid, around a region for measurement, said device comprising:

fluid enclosure portion for supplying a predetermined amount of fluid to said bladder and enclosing said fluid therein in order to wrap said blood pressure measurement cuff around said region for measurement; and pressure variation detection portion for detecting whether or not a relative variation in the pressure in said bladder has reached a predetermined level during the wrapping of said blood pressure measurement cuff around said region for measurement for blood pressure measurements, after said fluid is enclosed in said bladder by said fluid enclosure portion and prior to beginning the blood pressure measurements, wherein said relative variation is a calculated difference between the pressure in said bladder detected at a point in time and the pressure in said bladder detected at a subsequent point in time during the wrapping of said blood pressure measurement cuff around said region for measurement.

2. The blood pressure measurement cuff wrapping control device according to claim 1, further comprising:

wrapping stop operation portion for executing an operation for stopping the wrapping of said blood pressure measurement cuff around said region for measurement, when said pressure variation detection portion detects that said relative variation has reached the predetermined level.

3. The blood pressure measurement cuff wrapping control device according to claim 2, wherein said wrapping stop operation portion includes portion for announcing an instruction for stopping the wrapping to the outside.

4. The blood pressure measurement cuff wrapping control device according to claim 1, wherein
said pressure variation detection portion includes:
enclosure pressure detection portion for detecting the pressure within said bladder when said blood pressure measurement cuff is wrapped around said region for measurement, after said fluid is enclosed in said bladder by said fluid enclosure portion;
wrapping pressure detection portion for sequentially detecting the pressure within said bladder during further wrapping said blood pressure measurement cuff around said region for measurement for blood pressure measurements, after said enclosure pressure detection portion detects the pressure; and
determination portion for determining, each time said wrapping pressure detection portion detects the pressure, whether or not the difference between detected said pressure and the pressure detected by said enclosure pressure detection portion has reached said predetermined level.

5. The blood pressure measurement cuff wrapping control device according to claim 1, wherein
said pressure variation detection portion includes:
wrapping pressure detection portion for sequentially detecting the pressure within said bladder during further wrapping said blood pressure measurement cuff around said region for measurement for blood pressure measurements after said fluid is enclosed in said bladder by said fluid enclosure portion and then said blood pressure measurement cuff is wrapped and mounted around said region for measurement; and
determination portion for determining whether or not the variation per unit time in the pressure detected by said wrapping pressure detection portion has reached said predetermined level.

6. The blood pressure measurement cuff wrapping control device according to claim 5, wherein
said determination portion has portion for determining whether or not said variation per said unit time in the pressure detected by said wrapping pressure detection portion has reached a maximum.

7. The blood pressure measurement cuff wrapping control device according to claim 1, wherein
said blood pressure measurement cuff is manually wrapped around said region for measurement such that the wrapping size thereof in a radial direction for said region for measurement is reduced.

8. The blood pressure measurement cuff wrapping control device according to claim 1, wherein
the tension in said blood pressure measurement cuff is increased such that the wrapping size thereof in a radial direction for said region for measurement is reduced.

9. The blood pressure measurement cuff wrapping control device according to claim 1, wherein
said blood pressure measurement cuff further includes a securing bag which is inflated when supplied with said fluid in order to press said bladder for securing it around said region for measurement; and
the wrapping size of said blood pressure measurement cuff in a radial direction for said region for measurement is reduced by the effect of the inflation of said securing bag.

10. The blood pressure measurement cuff wrapping control device according to claim 1, further comprising:
circumferential length detection portion for detecting the circumferential length of said region for measurement; and
predetermined level determination portion for determining said predetermined level based on said circumferential length detected by said circumferential length detection portion.

11. A blood pressure measurement cuff wrapping control method for controlling wrapping of a blood pressure measurement cuff including a bladder, which is inflated when supplied with fluid, around a region for measurement, said method comprising:
a fluid enclosure step of supplying a predetermined amount of fluid to said bladder and enclosing it therein for said wrapping; and
a pressure change detection step of detecting whether or not a relative variation in the pressure in said bladder has reached a predetermined level during wrapping said blood pressure measurement cuff around said region for measurement for blood pressure measurements, after said fluid is enclosed in said bladder in said fluid enclosure step and prior to beginning the blood pressure measurements,
wherein said relative variation is a calculated difference between the pressure in said bladder detected at a point in time and the pressure in said bladder detected at a subsequent point in time during the wrapping of said blood pressure measurement cuff around said region for measurement.

12. The blood pressure measurement cuff wrapping control method according to claim 11, further comprising:
a wrapping stop operation step of performing an operation for stopping the wrapping of said blood pressure measurement cuff around said region for measurement, when it is detected that said relative variation has reached the predetermined level in said pressure change detection step.

* * * * *